United States Patent
Shi et al.

(10) Patent No.: US 11,377,674 B2
(45) Date of Patent: Jul. 5, 2022

(54) RECOMBINANT STRAIN EXPRESSING PHOSPHOLIPASE D AND APPLICATION THEREOF

(71) Applicant: JIANGNAN UNIVERSITY, Wuxi (CN)

(72) Inventors: Jinsong Shi, Wuxi (CN); Zhenghong Xu, Wuxi (CN); Jinsong Gong, Wuxi (CN); Haijuan Hou, Wuxi (CN); Xiaomei Zhang, Wuxi (CN); Heng Li, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 17/256,130

(22) PCT Filed: Aug. 2, 2018

(86) PCT No.: PCT/CN2018/098349
§ 371 (c)(1),
(2) Date: Dec. 24, 2020

(87) PCT Pub. No.: WO2020/019365
PCT Pub. Date: Jan. 30, 2020

(65) Prior Publication Data
US 2021/0123081 A1    Apr. 29, 2021

(30) Foreign Application Priority Data

Jul. 27, 2018 (CN) .......................... 201810844860.1

(51) Int. Cl.
| | |
|---|---|
| *C12N 15/75* | (2006.01) |
| *C12N 15/77* | (2006.01) |
| *C12N 15/81* | (2006.01) |
| *C12P 13/06* | (2006.01) |

(52) U.S. Cl.
CPC .............. *C12P 13/06* (2013.01); *C12N 15/75* (2013.01); *C12N 15/77* (2013.01); *C12N 15/815* (2013.01); *C12Y 301/04004* (2013.01)

(58) Field of Classification Search
CPC ... C12P 13/06; C12Y 301/04004; C12N 9/16; C12N 15/75; C12N 15/77; C12N 15/815
See application file for complete search history.

(56) References Cited

FOREIGN PATENT DOCUMENTS

| CN | 1408872 A | 4/2003 |
|---|---|---|
| CN | 107227284 A | 10/2017 |

OTHER PUBLICATIONS

Lee et al., Gen Bank accession No. ABY71835 Jan. 22, 2008.*
Lee et al., "Molecular cloning of the phospholipase D gene form *Streptomyces* sp. YU100 and its expression in *Escherichia coli*" The Journal of Microbiology, vol. 47, No. 1, pp. 116-122 (Feb. 20, 2009).

* cited by examiner

*Primary Examiner* — Delia M Ramirez
(74) *Attorney, Agent, or Firm* — SZDC Law P.C.

(57) ABSTRACT

The present invention provides a phospholipase D having an amino acid sequence as shown in SEQ ID NO. 1, and further provides a gene sequence encoding phospholipase D, which has a nucleotide sequence as shown in SEQ ID NO. 2. The present invention also provides a method for improving the expression level of phospholipase D by systematically engineering the expression elements. The method comprises screening and replacement of signal peptides, ribosome binding sites and promoters. The constructed recombinant plasmid is transformed into a host cell, and the recombinant strain is capable of successfully expressing phospholipase D. The phospholipase D of the present invention has a good phosphatidyl transferring ability, and can be used for synthesizing the product phosphatidylserine with lecithin and L-serine as substrates. The recombinant strain has good stability of enzyme activity and short fermentation period, which lays the foundation for large-scale industrial production.

5 Claims, 8 Drawing Sheets
Specification includes a Sequence Listing.

RECOMBINANT STRAIN EXPRESSING PHOSPHOLIPASE D AND APPLICATION THEREOF

This application is the National Stage Application of PCT/CN2018/098349, filed on Aug. 2, 2018, which claims priority to Chinese Patent Application No.: 201810844860.1, filed on Jul. 27, 2018, which is incorporated by reference for all purposes as if fully set forth herein.

FIELD OF THE INVENTION

The present invention relates to the field of biotechnologies, and more particularly to a recombinant strain expressing phospholipase D and application thereof.

DESCRIPTION OF THE RELATED ART

Phosatidylserine is a phospholipid that regulates the functional state of membrane proteins. It is found in both animal and plant tissues and used as a food additive to prevent Alzheimer's disease. Because of its positive effects in improving memory, preventing muscle pain, and treating depression, phosphatidylserine has received extensive attention in recent years. Under normal circumstances, phosphatidylserine can be obtained from animal and plant tissues by extraction and separation, or can be synthesized through a series of chemical reactions. However, due to the low content of phosphatidylserine in animal cells and plant tissues and the loss of phosphatidylserine caused during the separation and extraction, a low yield of the finally obtained phosphatidylserine is caused. Chemical synthesis of phosphatidylserine requires a series of complex chemical reactions, the process is cumbersome and causes environmental pollution. The phosphatidyl transfer reaction mediated by phospholipase D (PLD) is an effective method for the synthesis of phosphatidylserine. Due to the high conversion rate, mild reaction conditions, and environmental friendliness, the synthesis of phosphatidylserine by enzymatic method has received more and more attention.

Phospholipase D (EC 3.1.4.4) is widely present in a variety of organisms, including mammals, plants, yeasts and bacteria. Phospholipase D has become an important tool for the synthesis and modification of phospholipids. Some rare phospholipids synthesized by using phospholipase D are used as commercial reagents in laboratories, and phosphatidylserine is marketed as a food additive due to its known functions. Recently, it is proposed that various structurally and functionally related phospholipase D constitute the phospholipase D superfamily, including mammalian-, plant- and bacterium-derived phospholipase D. The members of the superfamily have the common features of two highly conserved sequences HxKxxxxD (where x represents any amino acid residue; defined as the HKD motif), which are considered to be the active center of phospholipase D. The tertiary structure of PMF PLD(PMF-PLD) from *Streptomyces* sp. is resolved. It is the first known phospholipase D sequence having a tertiary structure, the catalytic mechanism of which has also been further studied. Catalysis proceeds through a two-step (ping-pong mechanism) reaction. First, the histidine on the first HKD motif nucleophilically attacks the P—O bond on phosphatidylcholine to form a phosphatidylase intermediate. Then, the histidine on the second HKD activates the entered acceptor alcohol, and the activated acceptor alcohol attacks the transition-state intermediate to form the product phosphatidylserine (China Oils & Fats. 2016, 41, 80-84).

At present, studies have reported the heterologous expression of phospholipase D, and the most commonly used host is *Escherichia coli*. The phospholipase D gene from *Streptomyces* sp. is expressed in *E. coli* BL21(DE3)pLysE by Zambonelli et al., and the enzyme activity is determined to be about 0.005 U/mL by IPTG induction (Enzyme and Microbial Technology. 2003, 33, 676-688). In the food industry, *Bacillus subtilis* is generally recognized as safe (GRAS) expression host having a highly efficient extracellular secretion system. The protein expression and secretion to outside the cell can greatly simplify the downstream purification process. The phospholipase D coding gene from *E. coli* K12 is expressed in *Bacillus subtilis* DB104 by Lu et al., and the recombinant phospholipase D has an activity of 1.50 U/mL (China Biotechnology. 2008, 28, 56-60). *Corynebacterium glutamicum* is a gram-positive bacterium with a single-cell membrane. It is also considered as a GRAS strain. Due to the secretion efficiency of target protein, production and stability of secreted protein, and low extracellular hydrolase activity, *Corynebacterium glutamicum* has become a high-quality host for expressing foreign proteins.

At present, the research on phospholipase D in China and other countries mostly focused on the strain isolation and screening, the separation and purification of phospholipase D, and the physical and chemical properties. In molecular biology, there are relatively few studies on the cloning and expression of related genes.

SUMMARY OF THE INVENTION

In order to solve the above technical problems, an object of the present invention is to provide a recombinant strain expressing phospholipase D and use thereof. The present invention realizes the high-efficiency secretion and expression of phospholipase D through the engineering of signal peptide, RBS and promoter, and provides a recombinant plasmid comprising a gene of the present invention and a host cell comprising the recombinant plasmid, and a method for producing phosphatidylserine by using the recombinant strain.

A first object of the present invention is to provide a phospholipase D having an amino acid sequence as shown in SEQ ID NO. 1.

A second object of the present invention is to provide a gene sequence encoding the phospholipase D, which has a nucleotide sequence as shown in SEQ ID NO. 2.

A third object of the present invention is to provide a recombinant expression vector, a transgenic cell line or a transgenic recombinant strain comprising the nucleotide sequence as shown in SEQ ID NO. 2.

A fourth object of the present invention is to provide a recombinant plasmid expressing phospholipase D, which comprises a gene sequence as shown in SEQ ID NO. 2, a signal peptide gene allowing the extracellular expression of phospholipase D, a ribosome binding site for the expression of phospholipase D, and a promoter for the expression of phospholipase D, where the signal peptide gene has a nucleotide sequence as shown in SEQ ID NO. 3; the ribosome binding site has a nucleotide sequence as shown in SEQ ID NO. 4; and the promoter has a nucleotide sequence as shown in SEQ ID NO. 5.

Preferably, the starting plasmid used to construct the above recombinant plasmid is pDXW-10a, having a nucleotide sequence as shown in SEQ ID NO. 6.

In a specific embodiment of the present invention, the method for constructing the recombinant plasmid pDXW-wrpld4 includes the following steps:

(1) by using a plasmid containing the phospholipase D coding gene as a template, amplifying the phospholipase D coding gene by PCR with primers; by using the genome of *B. subtilis* 168 as a template, amplifying a signal peptide sequence by PCR with primers carrying RBS; fusing the signal peptide sequence containing RBS with the phospholipase D coding gene sequence by fusion PCR technology; and by using the genome of *B. subtilis* 168 as a template, amplifying a promoter sequence by PCR with designed primers;

(2) mutating the Kpn I restriction enzyme site GGTACC on the pDXW-10 multiple cloning site to GGAACC, and designing a Kpn I restriction enzyme site before the tac-M promoter to obtain the pDXW-10a plasmid;

(3) cloning the amplified product obtained in Step (1) into the pDXW-10a plasmid to construct a recombinant plasmid.

The present invention realizes the high-efficiency secretion and expression of phospholipase D through the engineering of signal peptide, RBS and promoter.

A fifth object of the present invention is to provide a recombinant strain expressing phospholipase D, in which the recombinant plasmid expressing phospholipase D is introduced.

Preferably, the host cell for the recombinant plasmid is *Bacillus subtilis, Pichia pastoris* or *Corynebacterium glutamicum*.

Preferably, a method for constructing the recombinant strain expressing phospholipase D includes the following steps:

electroporating the recombinant plasmid expressing phospholipase D into a host cell, and then culturing for 0.5-5 days (preferably 2-4 days) in a solid seed medium containing kanamycin at 20-60° C. (preferably 25-35° C.) until the transformants grow out; screening the positive transformant, inoculating the positive transformant in a liquid seed medium containing kanamycin, and culturing until OD562 is 10-40 (preferably 20-30).

A sixth object of the present invention is to provide use of the recombinant strain in the production of phosphatidylserine.

A seventh object of the present invention is to provide a method for producing phosphatidylserine, which includes the following steps:

catalytically reacting the substrates soybean lecithin and serine for 2-30 h at 30-70° C. in the presence of phospholipase D produced by the recombinant strain, to obtain phosphatidylserine.

Preferably, the reaction is carried out in the presence of $Ca^{2+}$.

More preferably, the concentration of $Ca^{2+}$ is 0.5-40 mM (preferably 10-20 mM, and more preferably 15 mM).

Preferably, the concentration ratio of soybean lecithin to serine is 1:1-1:8 (preferably 1:4-1:6, and more preferably 1:5).

Preferably, the reaction is carried out in a mixed system of organic-water phases, and the volume ratio of the organic phase to the water phase is 4:1-4:4.

More preferably, the organic phase is selected from the group consisting of n-hexane, ethyl acetate, chloroform, ether and toluene.

By means of the above technical solutions, the present invention has the following advantages.

The present invention provides a new phospholipase D and also provides a method for improving the expression level of phospholipase D by systematically engineering the expression elements, constructs a recombinant expression vector and a recombinant strain expressing phospholipase D, and provides a new method for producing phosphatidylserine. The recombinant strain constructed by the present invention shows phospholipase D activity, can successfully express phospholipase D, and the enzyme activity reaches 1.9 U/mL, which is 7.6 times higher than that of the starting strain without engineering. The phospholipase D of the present invention has a good phosphatidyl transferring ability, and is useful in the synthesis of the product phosphatidylserine with lecithin and L-serine as substrates. The recombinant strain has good stability of enzyme activity and short fermentation period, which lays the foundation for large-scale industrial production. The phospholipase D of the present invention has good phosphatidyl transferring ability, and thus has potential application value in the field of phosphatidylserine biosynthesis.

The above description is only a summary of the technical solutions of the present invention. To make the technical means of the present invention clearer and implementable in accordance with the disclosure of the specification, the preferred embodiments of the present invention will be described in detail with reference to the accompanying drawings.

DETAILED DESCRIPTION OF THE PREFERRED EMBODIMENTS

Figure 1:
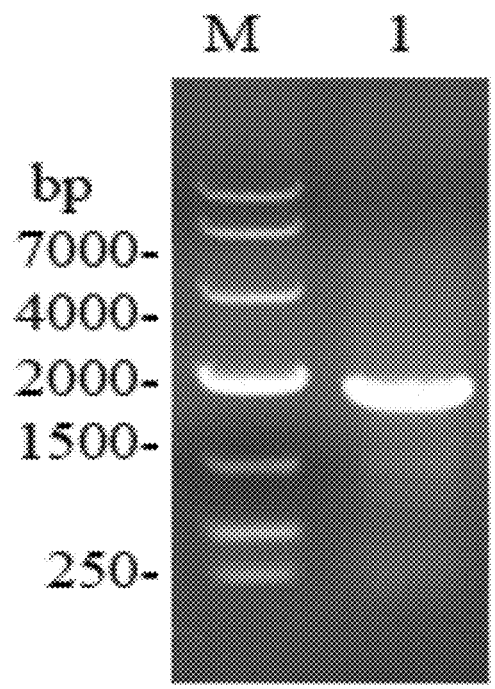
FIG. 1 is the electrophoretogram after PCR amplification of the phospholipase D coding gene. Lane M: 1,0000 bp DNA marker; and Lane 1: amplified phospholipase D gene.
Figure 2:
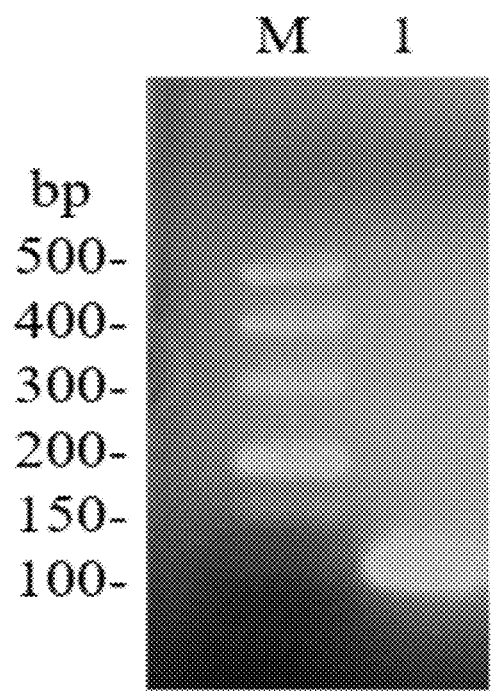
FIG. 2 is the electrophoretogram after PCR amplification of the WapA signal peptide coding gene containing a RBS site. Lane M: 500 bp DNA Marker; and Lane 1: amplified WapA gene.
Figure 3:
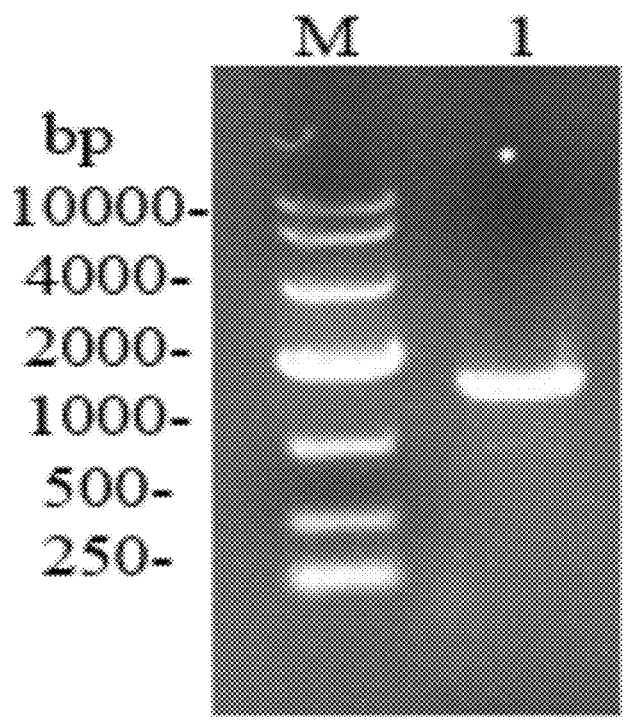
FIG. 3 is the electrophoretogram after fusion of the phospholipase D coding gene and the WapA signal peptide coding gene containing a RBS site by PCR. Lane M: 1,0000 bp DNA Marker; and Lane 1: amplified fusion gene.
Figure 4:
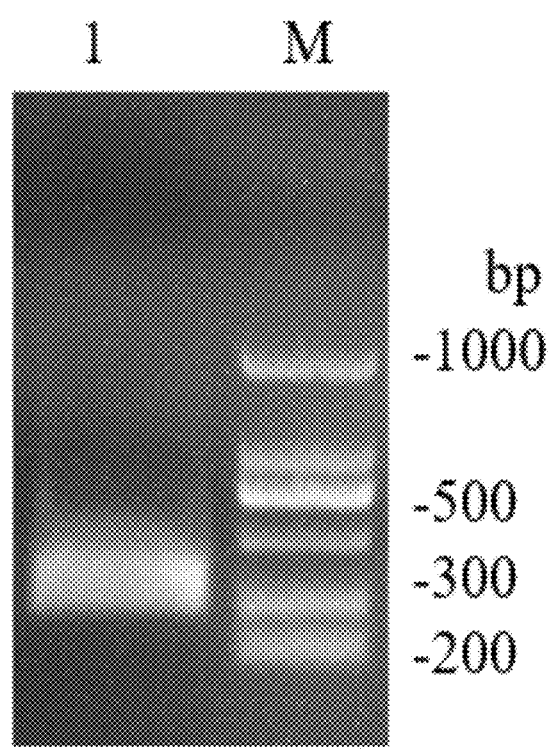
FIG. 4 is the electrophoretogram after PCR amplification of the pWapA promoter gene. Lane M: 500 bp DNA Marker; and Lane 1: amplified pWapA gene.
Figure 5:
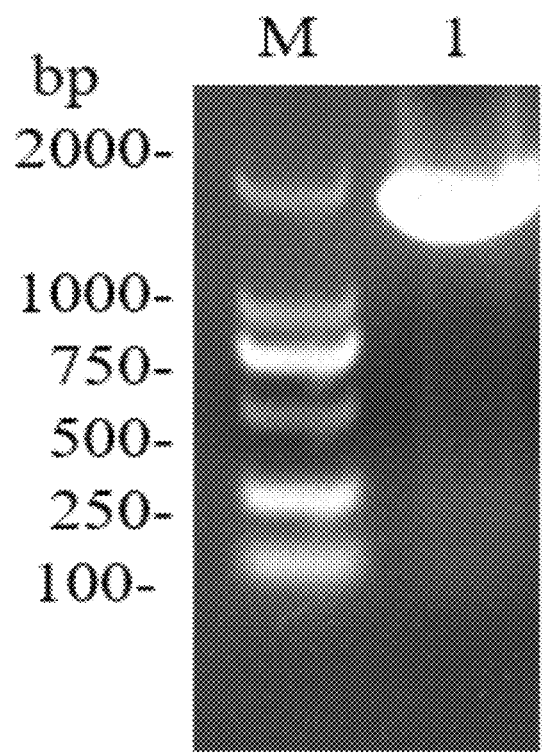
FIG. 5 shows the wrpld4 fragment after double enzyme digestion. Lane M: 1,0000 bp DNA Marker; and Lane 1: target gene after double enzyme digestion.
Figure 6:
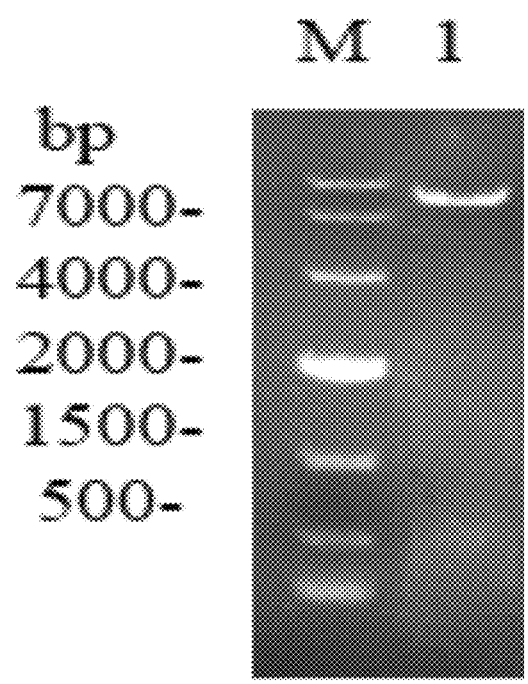
FIG. 6 is the electrophoretogram after double enzyme digestion of the pDXW-10a plasmid obtained by two one-step reverse PCR. Lane M: 1,0000 bp DNA Marker; and Lane 1: pDXW-10a plasmid gene after double enzyme digestion.
Figure 7:
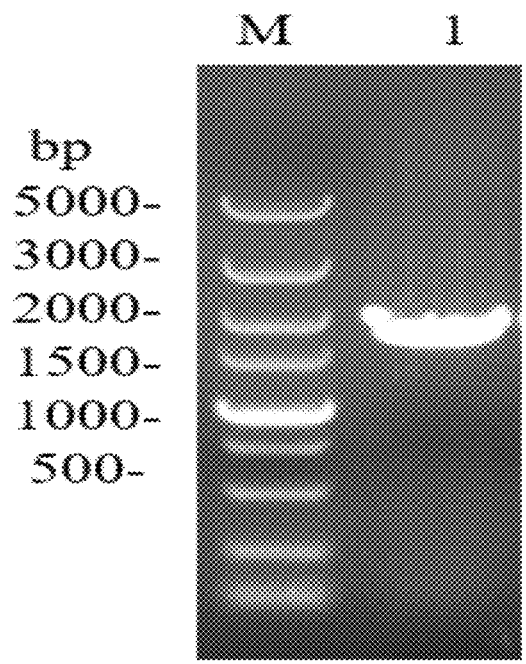
FIG. 7 is the electrophoretogram for verifying the amplified wrpld4 fragment on the pDXW-wrpld4 plasmid. Lane M: 1,0000 bp DNA Marker; and Lane 1: amplified wrpld4 fragment.
Figure 8:
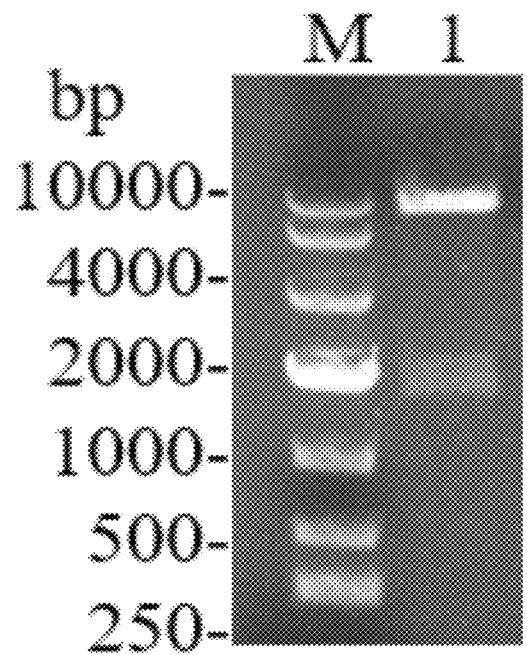
FIG. 8 is the electrophoretogram for verifying the recombinant plasmid pDXW-wrpld4 after double enzyme digestion. Lane M: 1,0000 bp DNA Marker; and Lane 1: pDXW-10a plasmid and wrpld4 fragment after double enzyme digestion.

The specific embodiments of the present invention will be described in further detail with reference to the accompanying drawings and specific embodiments. The following embodiments are intended to illustrate the present invention, instead of limiting the scope of the present invention.

Example 1

The present invention provides a phospholipase D, comprising 541 amino acids. The amino acid sequence is as shown in SEQ ID NO. 1. The gene encoding the phospholipase D has a nucleotide sequence as shown in SEQ ID NO. 2, with a full length of 1,623 nucleotides.

The present invention further provides a recombinant plasmid expressing phospholipase D, which comprises a nucleotide sequence as shown in SEQ ID NO. 2, a signal peptide gene allowing the extracellular expression of phospholipase D, a ribosome binding site for the expression of phospholipase D, and a promoter for the expression of phospholipase D, where the signal peptide gene has a nucleotide sequence as shown in SEQ ID NO. 3, with a full length of 96 nucleotides that encode 32 amino acids; the ribosome binding site (RBS) has a nucleotide sequence as shown in SEQ ID NO. 4, with a total of 15 nucleotides; and the promoter has a nucleotide sequence as shown in SEQ ID NO. 5, with a full length of 372 nucleotides.

Example 2

This example provides the construction of the recombinant plasmid pMA5-pld and its expression method in *Bacillus subtilis*. The specific steps are as follows:

(1) Amplification of Phospholipase D Coding Sequence

Using the recombinant plasmid pET-28a(+)-spld containing the phospholipase D coding gene as a template, the phospholipase D coding sequence was amplified with the designed primers (P1, P2):

```
Primer P1:
5'-CGGGATCCATGGCACGTCATCCGC-3'   (BamHI)

Primer P2:
5'-CGACGCGTTTAATCCTGACAAATA-3'   (MluI)
```

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 58.4° C. for 30 s, and extension at 72° C. for 1.5 min; and final extension at 72° C. for 10 min. The PCR product was identified by electrophoresis and extracted for recovery and purification. The product recovered in Step (1) was cloned into pMD19-T vector to construct a recombinant cloning plasmid. The plasmid was transformed into *E. coli* JM 109. Multiple transformants were picked into LB liquid medium (Amp$^r$) and incubated at 37° C. and 220 rpm for 10-12 h. The plasmid was extracted, and verified by PCR. The plasmid verified to be correct was sequenced.

(2) Construction of Recombinant Plasmid pMA5-pld

The pMA5 plasmid and the correct recombinant cloning plasmid containing the target gene obtained in Step (1) were both cleaved with BamH I and Mlu I at 37° C. for 3 hrs. The electrophoresis was performed for verification and the target gene and target plasmid were extracted and recovered. The recovered products were ligated overnight at 16° C. with T4 DNA ligase, and the ligated product was transformed into *E. coli* JM 109 competent cells. The cells were cultured overnight on solid LB medium containing ampicillin (100 mg/L). Multiple transformants were picked into LB liquid medium (Amp$^r$), and cultured at 37° C. and 220 rpm for 10-12 h. The plasmid was extracted and verified by PCR.

(3) Transformation of Recombinant Plasmid pMA5-pld into *B. Subtilis* WB600

The recombinant plasmid obtained in Step (2) was shipped to Shanghai Ruidi Sequencing Company for sequencing. The recombinant plasmid with the correct sequence was designated as pMA5-pld and transformed into *B. subtilis* WB600. The recombinant strain was cultured in TB medium for 36 h. The fermentation broth was centrifuged for 10 min at 12,000 rpm and 4° C., and then the cells were re-suspended in 4 mL buffer (40 mM Tris-HCl, 0.1% (v/v) Triton X-100, 15 mM CaCl$_2$). The cells were ultrasonically homogenized in an ice bath, and centrifuged. The supernatant was collected for activity determination. The enzyme activity of the recombinant *B. subtilis* WB600/pMA5-pld is 0.14 U/mL.

Example 3

This example provides the construction of the recombinant plasmid pMA5-npld and its expression method in *Bacillus subtilis*. The specific steps are as follows:

(1) Amplification of NprB Signal Peptide Sequence

By using the genome of *B. subtilis* 168 as a template, the NprB signal peptide sequence was amplified with the designed primers (P3, P4):

```
Primer P3:
5'-CGGGATCCCGCAACTTGACCAAGAC-3'   (BamH I)

Primer P4:
5'-TTGCGCGGATGACGTGCCATAGCAGCTGAGGCATGTGTTA-3'
```

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 54.6° C. for 30 s, and extension at 72° C. for 0.5 min; and final extension at 72° C. for 10 min. The PCR product was identified by electrophoresis and extracted for recovery and purification.

(2) Amplification of Phospholipase D Coding Sequence

Using the recombinant plasmid pET-28a(+)-spld containing the phospholipase D coding gene as a template, the phospholipase D coding sequence was amplified with the designed primers (P5, P6):

Primer P5:
5'-TAACACATGACTAGCAGCTATGGCACGTCATCCGCGCA-3'

Primer P6:
5'-CGACGCGTTTAATCCTGACAAATA-3' (Mlu I)

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 53° C. for 30 s, and extension at 72° C. for 1.5 min; and final extension at 72° C. for 10 min. The PCR product was identified by electrophoresis and extracted for recovery and purification.

(3) Fusion of Phospholipase D Gene and NprB Signal Peptide Sequence by Fusion PCR By using the extracted and purified phospholipase D sequence and NprB signal peptide sequence as templates, the two sequences were fused with Primers P3 and P6:

Primer P3:
5'-CGGGATCCCGCAACTTGACCAAGAC-3' (BamH I)

Primer P6:
5'-CGACGCGTTTAATCCTGACAAATA-3' (Mlu I)

The fusion process included two rounds of PCR reactions. First round: The PCR amplification reaction was carried out in a 47 μL system, in which 25 μL of PrimeSTAR® (Premix), 19 μL of ddH$_2$O, and 1.5 μL of each of the phospholipase D gene and WapA templates were added. The reaction conditions were as follows: pre-denaturation at 94° C. for 3 min; then 8 cycles of denaturation at 94° C. for 30 s, annealing at 50° C. for 30 s, and extension at 72° C. for 2 min; and final extension at 72° C. for 10 min. Second round: The PCR amplification reaction was carried out in a 50 μL system where 1.5 μL of each of the primers were added to the reaction system of the first round. The reaction conditions were as follows: pre-denaturation at 94° C. for 3 min; then 25 cycles of denaturation at 94° C. for 30 s, annealing at 56.2° C. for 30 s, and extension at 72° C. for 2 min; and final extension at 72° C. for 10 min. The PCR product was identified by electrophoresis and extracted for recovery and purification. The product recovered in Step (3) was cloned into pMD19-T vector to construct a recombinant cloning plasmid. The plasmid was transformed into *E. coli* JM 109. Multiple transformants were picked into LB liquid medium (Amp$^r$) and incubated at 37° C. and 220 rpm for 10-12 h. The plasmid was extracted, and verified by PCR.

(4) Construction of Recombinant Plasmid pMA5-npld

The pMA5 plasmid and the correct recombinant cloning plasmid containing the target gene were both cleaved with BamH I and Mlu I at 37° C. for 3 hrs. The electrophoresis was performed for verification and the target gene and target plasmid were extracted and recovered. The recovered products were ligated overnight at 16° C. with T4 DNA ligase, and the ligated product was transformed into *E. coli* JM 109 competent cells. The cells were cultured overnight on solid LB medium containing ampicillin (100 mg/L). Multiple transformants were picked into LB liquid medium containing ampicillin, and cultured at 37° C. and 220 rpm for 10-12 h. The plasmid was extracted. The recombinant plasmid was shipped to Shanghai Ruidi Sequencing Company for sequencing. The recombinant plasmid with the correct sequence was designated as pMA5-npld.

(5) Transformation of Recombinant Plasmid pMA5-npld into *B. Subtilis* WB600

The recombinant plasmid obtained in Step (4) was transformed into *B. subtilis* WB600. The recombinant strain was cultured in TB medium for 36 h. The fermentation broth was centrifuged for 10 min at 12000 rpm and 4° C. The fermentation supernatant containing phospholipase D was determined for enzyme activity. The enzyme activity of recombinant *B. subtilis* WB600/pMA5-pld was 0.16 U/mL.

Example 4

This example provides the construction of the recombinant plasmid pPIC3.5K-pld and its expression method in *Pichia pastoris*. The specific steps are as follows:

(1) Amplification of Phospholipase D Coding Sequence

Using the recombinant plasmid pET-28a(+)-spld containing the phospholipase D coding gene as a template, the phospholipase D coding sequence was amplified with the designed primers (P7, P8):

Primer P7:
5'-CGGGATCCATGGCACGTCATCCGC-3' (BamHI)

Primer P8:
5'-CGGAATTCTTAATCCTGACAAATA-3' (EcoRI)

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 58.4° C. for 30 s, and extension at 72° C. for 1.5 min; and final extension at 72° C. for 10 min. The PCR product was identified by electrophoresis and extracted for recovery and purification. The product recovered in Step (1) was cloned into pMD19-T vector to construct a recombinant cloning plasmid. The plasmid was transformed into *E. coli* JM 109. Multiple transformants were picked into LB liquid medium (Amp$^r$) and incubated at 37° C. and 220 rpm for 10-12 h. The plasmid was extracted, and verified by PCR. The plasmid verified to be correct was sequenced.

(2) Construction of Recombinant Plasmid pPIC3.5K-pld

The pPIC3.5K plasmid and the correct recombinant cloning plasmid containing the target gene were both cleaved with BamH I and EcoRI at 37° C. for 3 h. The electrophoresis was performed for verification and the target gene and target plasmid were extracted and recovered. The recovered products were ligated overnight at 16° C. with T4 DNA ligase, and the ligated product was transformed into *E. coli* JM 109 competent cells. The cells were cultured overnight on solid LB medium containing ampicillin (100 mg/L). Multiple transformants were picked into LB liquid medium containing ampicillin, and cultured at 37° C. and 220 rpm for 10-12 h. The plasmid was extracted.

(3) Transformation of Recombinant Plasmid pPIC3.5K-pld into *P. Pastoris* GS115

The recombinant plasmid obtained in Step (2) was shipped to Shanghai Ruidi Sequencing Company for sequencing. The recombinant plasmid with the correct sequence was designated as pPIC3.5K-pld. After linearization with Sal I restriction endonuclease, the plasmid was transformed into *P. pastoris* GS115 at 1500 v for 5 ms. The electroporated cell suspension was coated on MD medium, and incubated upside down in a constant-temperature incubator at 30° C. until the transformants were grown out. Then the transformants were transferred to YPD solid medium with different concentrations of antibiotic G418 sulfate and cultured for additional three days, to screen out high-copy strains on the plate with high concentration of antibiotic. The recombinant strain was inoculated into 10 mL YPD medium and incubated at 30° C. for 12 h and then inoculated into BMGY medium. After culturing for 24 h, the cells were harvested by centrifugation at 4500 rpm for 10 min and then resuspended in BMMY medium. Methanol with a final concentration of 5 g/L was added to the culture every 24 h for induction. After induction for 96 h, the fermentation broth was centrifuged for 10 min at 12000 rpm and 4° C. The cells were re-suspended in 4 mL buffer (40 mM Tris-HCl, 0.1% (v/v) Triton X-100, 15 mM $CaCl_2$). The cells were ultrasonically homogenized in an ice bath, and centrifuged. The supernatant was collected for activity determination. The enzyme activity of the recombinant P. pastoris GS115/pPIC3.5K-pld is 0.22 U/mL.

Example 5

This example provides the construction of the recombinant plasmid pPIC9K-pld and its expression method in Pichia pastoris. The specific steps are as follows:

(1) Amplification of Phospholipase D Coding Sequence

Using the recombinant plasmid pET-28a(+)-spld containing the phospholipase D coding gene as a template, the phospholipase D coding sequence was amplified with the designed primers (P9, P10):

```
Primer P9:
5'-CGGAATTCATGGCACGTCATCCGCGCAAA-3' (EcoRI)

Primer P10:
5'-AAGGAAAAAAGCGGCCGCTTAATCCTGACAAAT-3' (NotI)
```

The PCR amplification reaction was carried out in a 50 μL system, in which 25 μL of PrimeSTAR® (Premix), 20 μL of dd$H_2O$, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 59° C. for 30 s, and extension at 72° C. for 1.5 min; and final extension at 72° C. for 10 min. The PCR product was identified by electrophoresis and extracted for recovery and purification. The product recovered in Step (1) was cloned into pMD19-T vector to construct a recombinant cloning plasmid. The plasmid was transformed into E. coli JM 109. Multiple transformants were picked into LB liquid medium ($Amp^r$) and incubated at 37° C. and 220 rpm for 10-12 h. The plasmid was extracted, and verified by PCR. The plasmid verified to be correct was sequenced.

(2) Construction of Recombinant Plasmid pPIC9K-pld

The pPIC9K plasmid and the correct recombinant cloning plasmid containing the target gene were both cleaved with EcoRI and NotI at 37° C. for 3 h. The electrophoresis was performed for verification and the target gene and target plasmid were extracted and recovered. The recovered products were ligated overnight at 16° C. with T4 DNA ligase, and the ligated product was transformed into E. coli JM 109 competent cells. The cells were cultured overnight on solid LB medium containing ampicillin (100 mg/L). Multiple transformants were picked into LB liquid medium containing ampicillin, and cultured at 37° C. and 220 rpm for 10-12 h. The plasmid was extracted.

(3) Transformation of Recombinant Plasmid pPIC9K-pld into P. Pastoris GS115

The recombinant plasmid obtained in Step (2) was shipped to Shanghai Ruidi Sequencing Company for sequencing. The recombinant plasmid with the correct sequence was designated as pPIC9K-pld. After linearization with Sal I restriction endonuclease, the plasmid was transformed into P. pastoris GS115 at 1500 v for 5 ms. The electroporated cell suspension was coated on MD medium, and incubated upside down in a constant-temperature incubator at 30° C. until the transformants were grown out. Then the transformants were transferred to YPD solid medium with different concentrations of antibiotic G418 sulfate and cultured for additional three days, to screen out high-copy strains on the plate with high concentration of antibiotic. The recombinant strain was inoculated into 10 mL YPD medium and incubated 30° C. for 12 h and then inoculated into BMGY medium. After culturing for 24 h, the cells were harvested by centrifugation at 4500 rpm for 10 min and then resuspended in BMMY medium. Methanol with a final concentration of 5 g/L was added to the culture every 24 h for induction. After 96 h of induction, the fermentation broth was centrifuged for 10 min at 12000 rpm and 4° C. The fermentation supernatant containing phospholipase D was determined for enzyme activity. The enzyme activity of the recombinant P. pastoris GS115/pPIC9K-pld is 0.41 U/mL, which is lower than enzyme activity of phospholipase D expressed intracellularly.

Example 6

This example provides the construction of the recombinant plasmid pDXW-pld and its expression method in Corynebacterium glutamicum. The specific steps are as follows:

(1) Amplification of Phospholipase D Coding Sequence

Using the recombinant plasmid pET-28a(+)-spld containing the phospholipase D coding gene as a template, the phospholipase D coding sequence was amplified with the designed primers (P11, P12):

```
Primer P11:
5'-CGGAATTCATGGCACGTCATCCGCGCAAA-3' (EcoRI)

Primer P12:
5'-CCAAGCTTTTAATCCTGACAAATACCGCG-3' (Hind III)
```

The PCR amplification reaction was carried out in a 50 μL system, in which 25 μL of PrimeSTAR® (Premix), 20 μL of dd$H_2O$, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 57.2° C. for 30 s, and extension at 72° C. for 1.5 min; and final extension at 72° C. for 10 min. The PCR product was identified by electrophoresis and extracted for recovery and purification. The product recovered in Step (1) was cloned into pMD19-T vector to construct a recombinant cloning plasmid. The plasmid was transformed into E. coli JM 109. Multiple transformants were picked into LB liquid medium ($Kan^r$) and incubated at 37° C. and 220 rpm for 10-12 h. The plasmid was extracted, and verified by PCR. The plasmid verified to be correct was sequenced.

(2) Construction of Recombinant Plasmid pDXW-pld

The pDXW-10 plasmid and the correct recombinant cloning plasmid containing the target gene were both cleaved with EcoR I and Hind III at 37° C. for 3 h. The electrophoresis was performed for verification and the target gene and target plasmid were extracted and recovered. The recovered products were ligated overnight at 16° C. with T4 DNA ligase, and the ligated product was transformed into E. coli JM 109 competent cells. The cells were cultured overnight on solid LB medium containing kanamycin (50 mg/L). Multiple transformants were picked into LB liquid medium containing kanamycin, and cultured at 37° C. and 220 rpm for 10-12 h. The plasmid was extracted.

(3) Transformation of Recombinant Plasmid pDXW-pld into C. glutamicum ATCC 13032

The recombinant plasmid obtained in Step (2) was shipped to Shanghai Ruidi Sequencing Company for sequencing. The recombinant plasmid with the correct sequence was designated as pDXW-pld. The recombinant plasmid was electroporated into C. glutamicum ATCC 13032 at 1900 V for 5 ms. The cells were coated on a solid seed medium containing kanamycin (50 mg/L), and incubated upside down in an incubator at 30° C. until the transformants were grown out. Positive transformants were screened out by PCR verification, and inoculated into a liquid seed medium containing kanamycin (50 mg/L), and incubated to OD562=25. The fermentation broth was centrifuged for 10 min at 12000 rpm and 4° C. The cells were re-suspended in 4 mL buffer (40 mM Tris-HCl, 0.1% (v/v) Triton X-100, 15 mM CaCl$_2$). The cells were ultrasonically homogenized in an ice bath, and centrifuged. The supernatant was collected for activity determination. The enzyme activity of the recombinant C. glutamicum ATCC 13032/pDXW-pld is 0.25 U/mL.

Example 7

This example provides the construction of the recombinant plasmid pDXW-pld4 and its expression method in Corynebacterium glutamicum. The specific steps are as follows:

(1) Using the recombinant plasmid pET-28a(+)-spld containing the phospholipase D coding gene as a template, the phospholipase D coding sequence was amplified with the designed primers (P13, P14):

```
Primer P13:
5'-AGCCGATGTACTAGCAGCTATGGCACGTCATCCGCGCA-3'

Primer P14:
5'-CCAAGCTTTTAATCCTGACAAATACCGCG-3' (Hind III)
```

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 57° C. for 30 s, and extension at 72° C. for 1.5 min; and final extension at 72° C. for 10 min. The PCR product was identified by electrophoresis and extracted for recovery and purification.

(2) By using the genome of B. subtilis 168 as a template, the WapA signal peptide sequence was amplified with the designed primers (P15, P16):

```
Primer P15:
5'-CGGAATTCTGAAAAAAGAAAGAGG-3' (EcoR I)

Primer P16:
5'-TTGCGCGGATGACGTGCCATAGCAGCTGCTAGTACATCGGCT-3'
```

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 53° C. for 30 s, and extension at 72° C. for 0.5 min; and final extension at 72° C. for 10 min. The PCR product was identified by electrophoresis and extracted for recovery and purification.

(3) By using the extracted and purified phospholipase D sequence and WapA signal peptide sequence as templates, the two sequences were fused with Primers P14 and P15:

```
Primer P14:
5'-CCAAGCTTTTAATCCTGACAAATACCGCG-3' (Hind III)

Primer P15:
5'-CGGAATTCAAAAAAAGAAAGAGG-3' (EcoR I)
```

The fusion process included two rounds of PCR reactions. First round: The PCR amplification reaction was carried out in a 47 μL system, in which 25 μL of PrimeSTAR® (Premix), 19 μL of ddH$_2$O, and 1.5 μL of each of the phospholipase D gene and WapA templates were added. The reaction conditions were as follows: pre-denaturation at 94° C. for 3 min; then 8 cycles of denaturation at 94° C. for 30 s, annealing at 50° C. for 30 s, and extension at 72° C. for 2 min; and final extension at 72° C. for 10 min. Second round: The PCR amplification reaction was carried out in a 50 μL system where 1.5 μL of each of the primers were added to the reaction system of the first round. The reaction conditions were as follows: pre-denaturation at 94° C. for 3 min; then 25 cycles of denaturation at 94° C. for 30 s, annealing at 55° C. for 30 s, and extension at 72° C. for 2 min; and final extension at 72° C. for 10 min. The PCR product was identified by electrophoresis and extracted for recovery and purification. The product recovered in Step (3) was cloned into pMD19-T vector to construct a recombinant cloning plasmid. The plasmid was transformed into E. coli JM 109. Multiple transformants were picked into LB liquid medium (Kan$^r$) and incubated at 37° C. and 220 rpm for 10-12 h. The plasmid was extracted, and verified by PCR. The plasmid verified to be correct was sequenced.

(4) Construction of Recombinant Plasmid pDXW-pld4

The pDXW-10 plasmid and the correct recombinant cloning plasmid containing the target gene were both cleaved with EcoR I and Hind III at 37° C. for 3 h. The electrophoresis was performed for verification and the target gene and target plasmid were extracted and recovered. The recovered products were ligated overnight at 16° C. with T4 DNA ligase, and the ligated product was transformed into E. coli JM 109 competent cells. The cells were cultured overnight on solid LB medium containing kanamycin (50 mg/L). Multiple transformants were picked into LB liquid medium containing kanamycin, and cultured at 37° C. and 220 rpm for 10-12 h. The plasmid was extracted.

(5) Transformation of Recombinant Plasmid pDXW-pld4 into C. Glutamicum ATCC 13032

The recombinant plasmid obtained in Step (4) was shipped to Shanghai Ruidi Sequencing Company for sequencing. The recombinant plasmid with the correct sequence was designated as pDXW-pld. The recombinant plasmid was electroporated into C. glutamicum ATCC 13032 at 1900 v for 5 ms. The cells were coated on a solid seed medium containing kanamycin (50 mg/L), and incubated upside down in an incubator at 30° C. until the transformants were grown out. Positive transformants were screened out by PCR verification, and inoculated into a liquid seed medium containing kanamycin (50 mg/L), and incubated to OD562=25. The fermentation broth was centrifuged for 10 min at 12000 rpm and 4° C. The supernatant was collected for activity determination. The enzyme activity of the recombinant C. glutamicum ATCC 13032/pDXW-pld4 is 0.91 U/mL.

Figure 9:
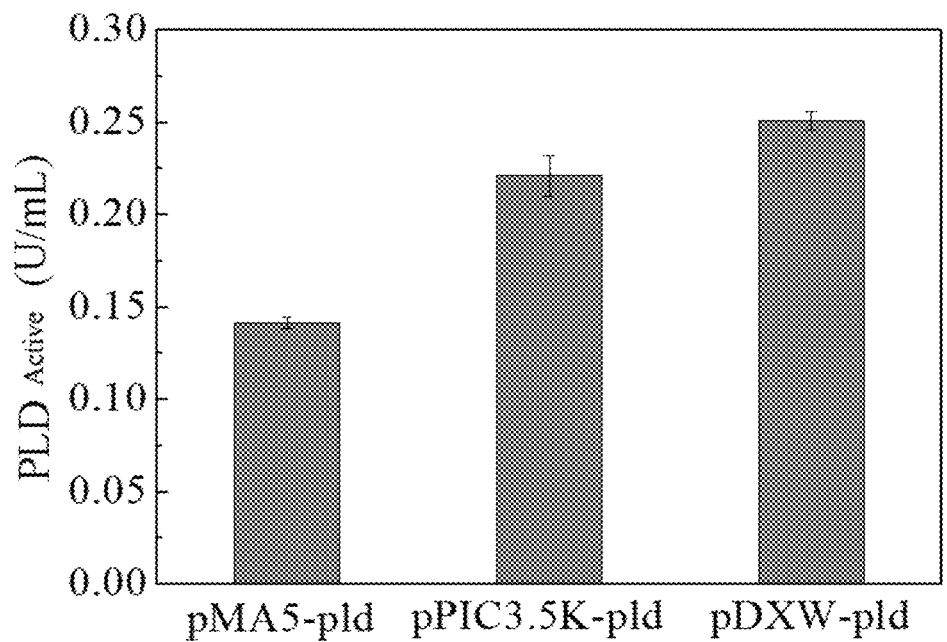
FIG. 9 shows the results of the enzyme activity test of phospholipase D after intracellular expression by *Bacillus subtilis, Pichia pastoris*, and *Corynebacterium glutamicum*.
Figure 10:
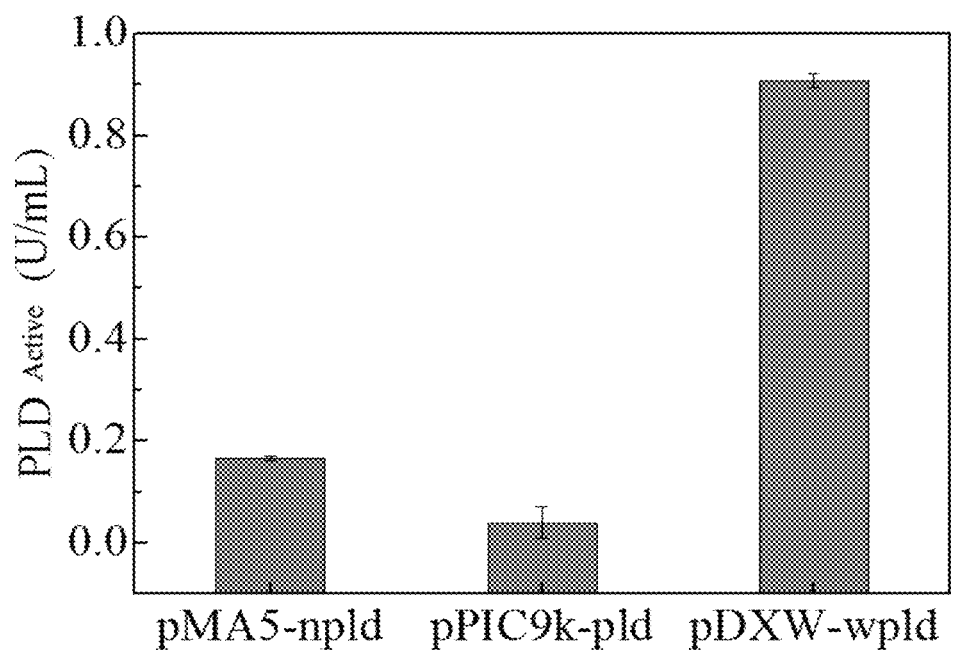
FIG. 10 shows the results of the enzyme activity test of phospholipase D after extracellular secretion and expression by *Bacillus subtilis, Pichia pastoris*, and *Corynebacterium glutamicum*.

In the above examples, the heterologous expression of phospholipase D in Bacillus subtilis, Pichia pastoris, and Corynebacterium glutamicum is achieved, and the enzyme activities of the recombinant strains are 0.14 U/mL, 0.22 U/mL, and 0.25 U/mL, respectively (FIG. 9). The use of signal peptides realizes the secretory expression of phospholipase D in Bacillus subtilis, Pichia pastoris, and Corynebacterium glutamicum. The enzyme activity of the recombinant strains is shown in FIG. 10. Because phospholipase D shows a highest hydrolysis activity of 0.91 U/mL in Corynebacterium glutamicum, Corynebacterium glutamicum is taken as the optimal expression host and WapA is the optimal signal peptide.

Example 8

This example provides the construction of the recombinant plasmid pDXW-rpld4 added with RBS and its expression method in Corynebacterium glutamicum. The specific steps are as follows:

(1) Using the recombinant plasmid pET-28a(+)-spld containing the phospholipase D coding gene as a template, the phospholipase D coding sequence was amplified with the designed primers (P13, P14):

```
Primer P13:
5'-AGCCGATGTACTAGCAGCTATGGCACGTCATCCGCGCA-3'

Primer P14:
5'-CCAAGCTTTTAATCCTGACAAATACCGCG-3' (Hind III)
```

The PCR amplification reaction was carried out in a 50 µL system, in which 25 µL of PrimeSTAR® (Premix), 20 µL of ddH₂O, 2 µL of template DNA, and 1.5 µL of each of the upstream and downstream primers were added. The reaction conditions were as follows: pre-denaturation at 94° C. for 3 min; then 30 cycles of denaturation at 94° C. for 30 s, annealing at 57° C. for 30 s, and extension at 72° C. for 1.5 min; and final extension at 72° C. for 10 min. The PCR product was identified by electrophoresis and extracted for recovery and purification.

(2) By using the genome of B. subtilis 168 as a template, a WapA signal peptide sequence containing the RBS sequence (AGAAGGAGATATACC) was amplified with the designed primers (P16, P17):

```
Primer P16:
5'-TTGCGCGGATGACGTGCCATAGCAGCTGCTAGTACATCGGCT-3'

Primer P17:
5'-CGGAATTCAGAAGGAGATATACCAAAAAAAGAAAGAGG-3'

(EcoR I)
```

The PCR amplification reaction was carried out in a 50 µL system, in which 25 µL of PrimeSTAR® (Premix), 20 µL of ddH₂O, 2 µL of template DNA, and 1.5 µL of each of the upstream and downstream primers were added. The reaction conditions were as follows: pre-denaturation at 94° C. for 3 min; then 30 cycles of denaturation at 94° C. for 30 s, annealing at 53.5° C. for 30 s, and extension at 72° C. for 0.5 min; and final extension at 72° C. for 10 min. The PCR product was identified by electrophoresis and extracted for recovery and purification.

(3) By using the extracted and purified phospholipase D sequence and WapA signal peptide sequence containing the RBS sequence as templates, the two sequences were fused with Primers P14 and P17:

```
Primer P14:
5'-CCAAGCTTTTAATCCTGACAAATACCGCG-3' (Hind III)

Primer P17:
5'-CGGAATTCAGAAGGAGATATACCAAAAAAAGAAAGAGG-3'

(EcoR I)
```

The fusion process included two rounds of PCR reactions. First round: The PCR amplification reaction was carried out in a 47 µL system, in which 25 µL of PrimeSTAR® (Premix), 19 µL of ddH₂O, and 1.5 µL of each of the phospholipase D gene and WapA templates were added. The reaction conditions were as follows: pre-denaturation at 94° C. for 3 min; then 8 cycles of denaturation at 94° C. for 30 s, annealing at 50° C. for 30 s, and extension at 72° C. for 2 min; and final extension at 72° C. for 10 min. Second round: The PCR amplification reaction was carried out in a 50 µL system where 1.5 µL of each of the primers were added to the reaction system of the first round. The reaction conditions were as follows: pre-denaturation at 94° C. for 3 min; then 25 cycles of denaturation at 94° C. for 30 s, annealing at 55.5° C. for 30 s, and extension at 72° C. for 2 min; and final extension at 72° C. for 10 min. The PCR product was identified by electrophoresis and extracted for recovery and purification. The product recovered in Step (3) was cloned into pMD19-T vector to construct a recombinant cloning plasmid. The plasmid was transformed into E. coli JM 109. Multiple transformants were picked into LB liquid medium (Kan^r) and incubated at 37° C. and 220 rpm for 10-12 h. The plasmid was extracted, and verified by PCR. The plasmid verified to be correct was sequenced.

(4) Construction of Recombinant Plasmid pDXW-rpld4

The pDXW-10 plasmid and the correct recombinant cloning plasmid containing the target gene were both cleaved with EcoR I and Hind III at 37° C. for 3 h. The electrophoresis was performed for verification and the target gene and target plasmid were extracted and recovered. The recovered products were ligated overnight at 16° C. with T4 DNA ligase, and the ligated product was transformed into E. coli JM 109 competent cells. The cells were cultured overnight on solid LB medium containing kanamycin (50 mg/L). Multiple transformants were picked into LB liquid medium containing kanamycin, and cultured at 37° C. and 220 rpm for 10-12 h. The plasmid was extracted.

(5) Transformation of Recombinant Plasmid pDXW-rpld4 into C. Glutamicum ATCC 13032

The recombinant plasmid obtained in Step (4) was shipped to Shanghai Ruidi Sequencing Company for sequencing. The recombinant plasmid with the correct sequence was designated as pDXW-pld. The recombinant plasmid was electroporated into C. glutamicum ATCC 13032 at 1900 v for 5 ms. The cells were coated on a solid seed medium containing kanamycin (50 mg/L), and incubated upside down in an incubator at 30° C. until the transformants were grown out. Positive transformants were screened out by PCR verification, and inoculated into a liquid seed medium containing kanamycin (50 mg/L), and incubated to OD562=25. The fermentation broth was centrifuged for 10 min at 12000 rpm and 4° C. The supernatant was collected for activity determination. The enzyme activity of the recombinant C. glutamicum ATCC 13032/pDXW-rpld4 is 1.06 U/mL, which is increased by 16% compared with the recombinant strain without RBS.

Example 9

This example provides the construction of the recombinant plasmid pDXW-wrpld4 in which the tac-M promoter is replaced by the pWapA promoter, and its expression method in Corynebacterium glutamicum. The specific steps are as follows:

(1) By using the genome of B. subtilis 168 as a template, the pWapA promoter sequence was amplified with the designed primers (P18, P19):

```
Primer P18:
5'-GGGGTACCATTTTTATCAACGAAATTTATTT-3' (Kpn I)

Primer P19:
5'-CGGAATTCTTCCTCTCTCCTTTTGTAATA-3' (EcoRI)
```

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 58° C. for 30 s, and extension at 72° C. for 0.5 min; and final extension at 72° C. for 10 min. The PCR product was identified by electrophoresis and extracted for recovery and purification.

(2) By using the pDXW-10 plasmid as a template, the Kpn I restriction site GGTACC on the multiple cloning site in the plasmid was mutated to GGAACC with the designed primers (P20, P21, P22, P23), and a Kpn I restriction site was designed before the tac-M promoter. The engineered pDXW-10 plasmid was designated as pDXW-10a plasmid.

```
Primer P20:
5'-GCCTCGAGGGAACCAGATCTCCGCGGCTTAA-3'

Primer P21:
5'-AGATCTGGTTCCCTCGAGGCGGCCGCCCAT-3'

Primer P22:
5'-TCATAACGGTACCGGCAAATATTCTGAAATGAGCTGTTG-3'

Primer P23:
5'-ATTTCAGAATATTTGCCGGTACCGTTATGATGTCGGCGCA-3'
```

The PCR amplification reaction was carried out in a 50 μL system, in which 25 μL of PrimeSTAR® (Premix), 20 μL of ddH$_2$O, 2 μL of template DNA, and 1.5 μL of each of the upstream and downstream primers were added. The reaction conditions were as follows: pre-denaturation at 94° C. for 3 min; then 30 cycles of denaturation at 94° C. for 30 s, annealing at 59° C. for 30 s, and extension at 72° C. for 10 min; and final extension at 72° C. for 10 min. The PCR product was identified by electrophoresis and extracted for recovery and purification.

(3) Construction of Recombinant Plasmid pDXW-wrpld4

The pDXW-10a plasmid (SEQ ID NO.6) was cleaved for 3 h with Kpn I and Hind at 37° C. Then electrophoresis was performed for verification and the target plasmid were extracted and recovered. The correct recombinant cloning plasmid containing the target gene in Example 9 was cleaved for 3 h with Kpn I and EcoRI at 37° C. Then electrophoresis was performed for verification and the target gene were extracted and recovered. The pWapA fragment obtained in Step (1) was cleaved for 3 h with EcoRI and Hind III at 37° C. Then electrophoresis was performed for verification and the pWapA gene were extracted and recovered. The three fragments of recovered products were ligated overnight at 16° C. with T4 DNA ligase, and the ligated product was transformed into E. coli JM 109 competent cells. The cells were cultured overnight on solid LB medium containing kanamycin (50 mg/L). Multiple transformants were picked into LB liquid medium containing kanamycin, and cultured at 37° C. and 220 rpm for 10-12 h. The plasmid was extracted.

(4) Transformation of Recombinant Plasmid pDXW-wrpld4 into C. Glutamicum ATCC 13032

The recombinant plasmid obtained in Step (3) was shipped to Shanghai Ruidi Sequencing Company for sequencing. The recombinant plasmid with the correct sequence was designated as pDXW-wrpld4. The recombinant plasmid was electroporated into C. glutamicum ATCC 13032 at 1900 v for 5 ms. The cells were coated on a solid seed medium containing kanamycin (50 mg/L), and incubated upside down in an incubator at 30° C. until the transformants were grown out. Positive transformants were screened out by PCR verification, and inoculated into a liquid seed medium containing kanamycin (50 mg/L), and incubated to OD562=25. The fermentation broth was centrifuged for 10 min at 12000 rpm and 4° C. The supernatant was collected for activity determination. The enzyme activity of the recombinant C. glutamicum ATCC 13032/pDXW-wrpld4 is 1.3 U/mL.

In this example, by means of heterologous expression, addition of signal peptide and RBS, and replacement of promoter, high-efficiency expression of phospholipase D is achieved in Corynebacterium glutamicum. Recombinant C. glutamicum ATCC 13032/pDXW-wrpld4 in the optimized fermentation medium has an enzyme activity 1.9 U/mL, which is 7.6 times that of the unengineered recombinant C. glutamicum ATCC 13032/pDXW-pld.

In the above examples of the present invention, the process for determining the hydrolysis activity of phospholipase D was as follows:

A 100 μL reaction system containing 60 μL substrate lecithin solution (preheated for 5 min) and 40 μL enzyme solution was thoroughly mixed and reacted at 60° C. for 20 min. 50 μL of a stop solution was added to terminate the reaction. The system was placed in boiling water for 5 min and then immediately cooled on ice. The system was centrifuged at 6000 rpm for 5 min. All the supernatant was pipetted and added with 60 μL choline oxidase, 200 μL phenol solution, 200 μL 4-aminoantipyrine solution and 40 μL peroxidase, fully mixed and reacted at 37° C. for 20 min. After reaction, the absorbency at OD505 nm was determined, and the enzyme activity was calculated according to the standard curve.

The molecular weight of phospholipase D protein was also tested in the present invention, and the process was as follows.

Figure 11:
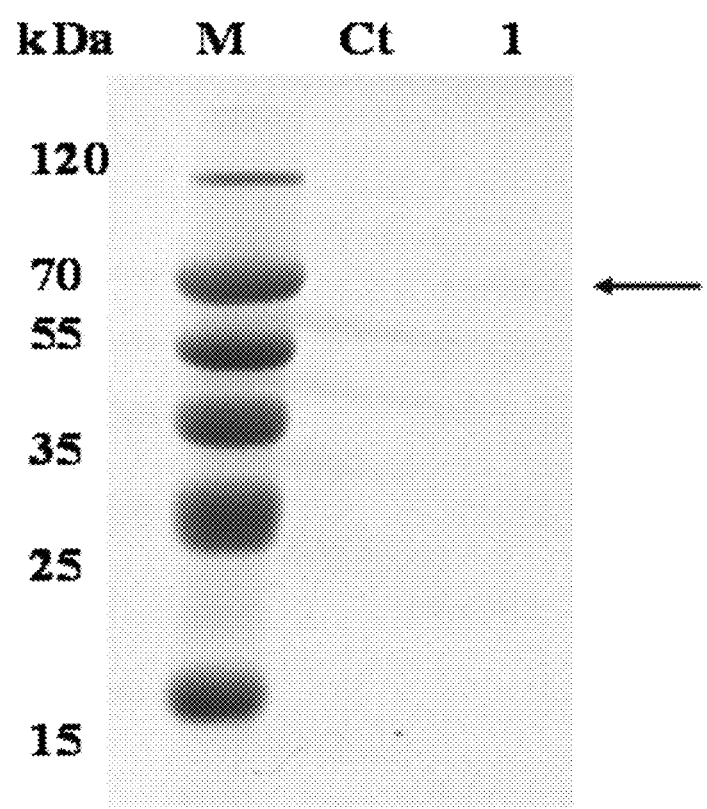
FIG. 11 is an SDS-PAGE electrophoretogram of recombinant *C. glutamicum* ATCC13032/pDXW-wrpld4. Lane 1: Protein Marker; Lane 2: Blank control; Lane 3: phospholipase D protein band.

The separation gel and concentration gel were prepared according to the composition of 10% separation gel and concentration gel. Then 80 μL sample was added to 20 μL 5× loading buffer, mixed well and stood in a boiling water bath for 5 min to denature the protein. The sample was loaded according to the protein concentration and a protein marker was added. The upper concentration gel was applied with a voltage of 80 V (about 30 min) and the lower separation gel was applied with a voltage of 100 V. When the sample reached to about 1 cm from the bottom of the separation gel, the power was turned off. Subsequently, the sample was rinsed with distilled water, dried and decolored, and the molecular weight of phospholipase D protein was determined. The SDS-PAGE results show (FIG. 11) that the molecular weight of the phospholipase D expressed in Example 9 of the present invention is 60 kDa.

Example 10

This example provides a method for producing phosphatidylserine (PS).

The initial conversion process was as follows. Soybean lecithin (PC50) was dissolved in 8 mL ethyl acetate to give a concentration of 8 mg/mL and used as the organic phase, and 160 mg L-serine was dissolved in 4 mL phospholipase D crude enzyme solution and used as the aqueous phase. After the organic phase and the aqueous phase were ultrasonically mixed fully, and then reacted for 12 h with shaking at 120 rpm at 40° C.

20 mL mixed solution of chloroform/methanol (volume ratio 2/1) and 3 mL ultrapure water were added to the reaction solution, and centrifuged at 2500 rpm for 5 min. The lower solution was removed, and the remainder was concentrated by a vacuum centrifugal concentrator, dissolved in 2 mL n-hexane/isopropanol (volume ratio 1/1), and filtered through a 0.22 μm organic membrane. The product phosphatidylserine was detected and analyzed by HPLC.

In order to obtain the most desirable conversion rate, the conversion conditions were optimized in this example. The conversion process was optimized from the selection of organic solvent, the volume ratio of organic phase to aqueous phase, the ratio of substrate concentration, the conversion temperature, the conversion time and the concentration of calcium ions.

(1) Selection of Organic Solvent

Figure 12:
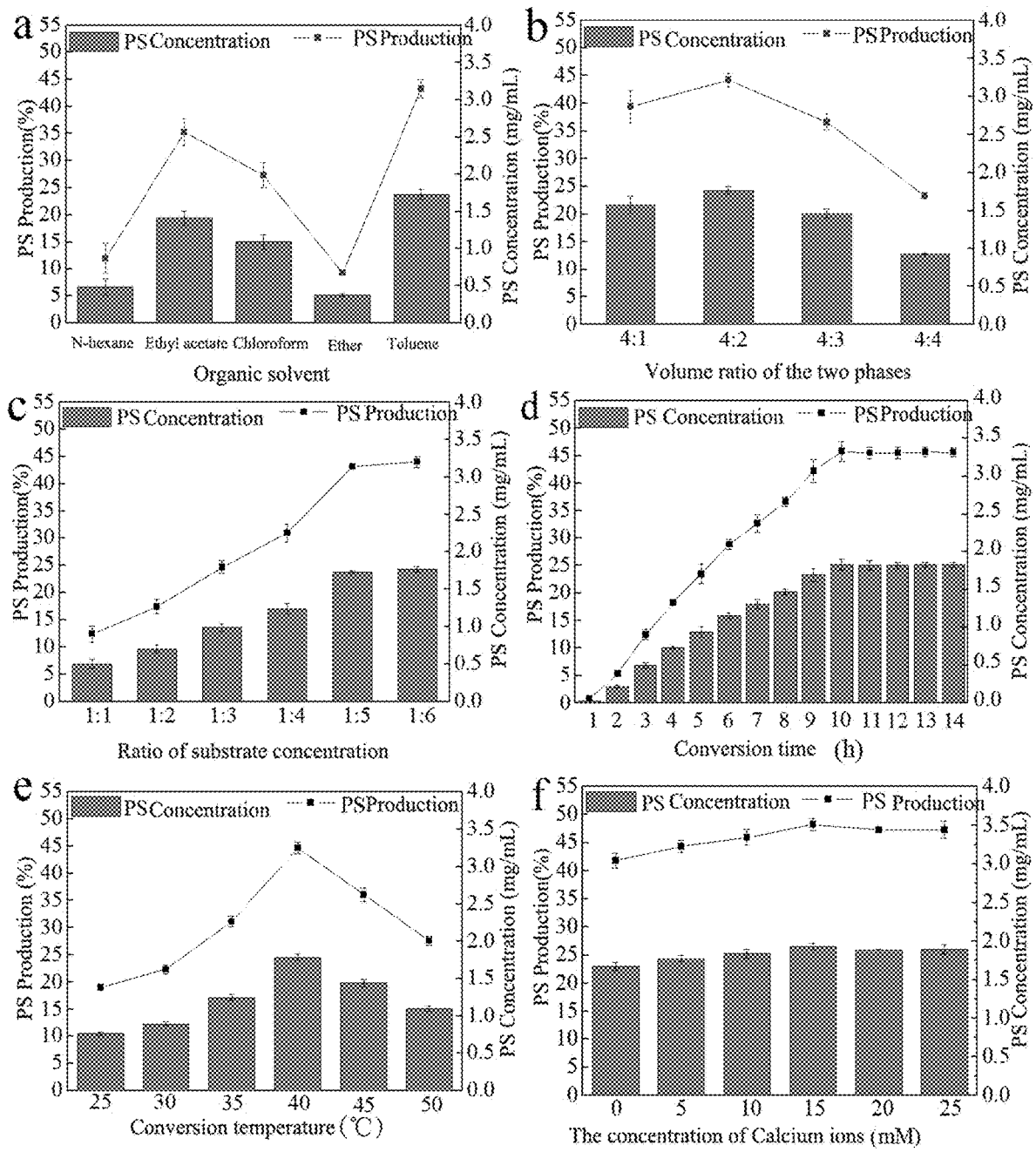
FIG. 12 shows the test results of conversion rate for phosphatidylserine produced under different conditions.
Figure 13:
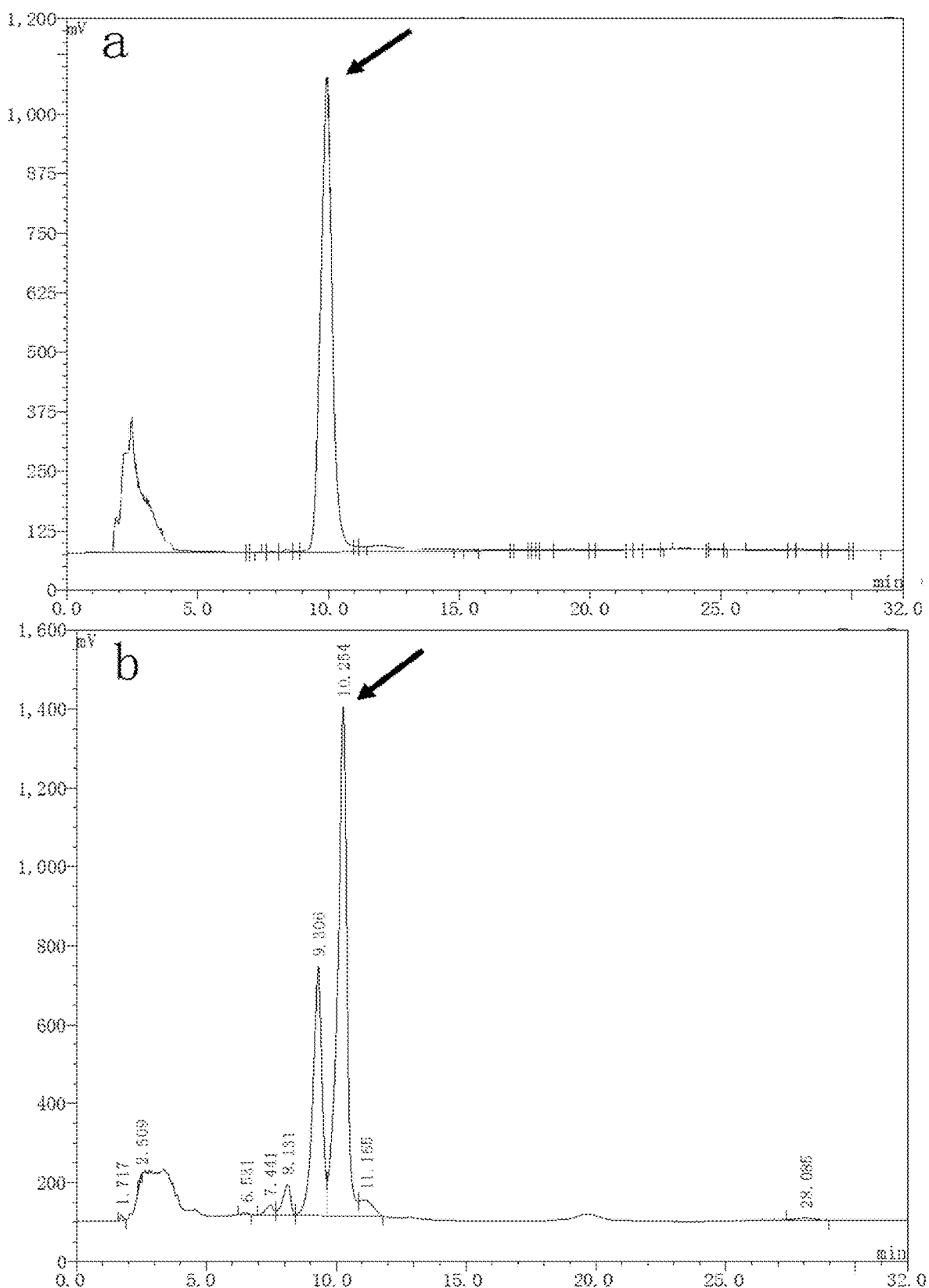
FIG. 13 is the HPLC chromatogram of phosphatidylserine catalytically produced with the substrates lecithin and L-serine in the presence of phospholipase D. a: phosphatidylserine standard sample; b: phosphatidylserine in the conversion solution sample.

Ethyl acetate in the initial conversion conditions was replaced by the same volume of n-hexane, chloroform, ether or toluene. Through detection and analysis by HPLC, when the organic phase is toluene, the rate of conversion to phosphatidylserine is the highest and is 43.3% (FIG. 12a), so toluene can be used as the optimal organic phase.

(2) Volume Ratio of Organic Phase to Aqueous Phase

The organic phase in the initial conversion conditions was replaced by toluene, and the volume ratio of the organic phase to the aqueous phase was set to 4:1, 4:2, 4:3 or 4:4 respectively, and the other conversion conditions remained unchanged. The influence of the volume ratio of the two phases on the conversion rate was investigated. When the volume ratio of the organic phase to the aqueous phase is 4:2, the rate of conversion to phosphatidylserine is the highest and is 44.5% (FIG. 12b), so the volume ratio of the two phases of 4:2 is the optimal ratio.

(3) Ratio of Substrate Concentration

PC50 was dissolved in 8 mL toluene to give a concentration of 8 mg/mL and used as the organic phase, and L-serine was dissolved in 4 mL crude enzyme solution to give a concentration of 8, 16, 24, 32, 40, or 48 mg/mL respectively and used as the aqueous phase. The organic phase and the aqueous phase were ultrasonically mixed thoroughly, and reacted for 12 h with shaking at 120 rpm at 40° C. The influence of different ratios of substrate concentration on the conversion rate was investigated. When the PC50 concentration is 8 mg/mL and the L-serine concentration is 40 mg/mL, the rate of conversion to phosphatidylserine is the highest, reaching 43.2% (FIG. 12c), so 1:5 is the optimal ratio of substrate concentration.

(4) Conversion Temperature

PC50 was dissolved in 8 mL toluene to give a concentration of 8 mg/mL and used as the organic phase, and L-serine was dissolved in 4 mL phospholipase D crude enzyme solution to give a concentration of 40 mg/mL and used as the aqueous phase. The organic phase and the aqueous phase were ultrasonically mixed thoroughly, and reacted for 12 h with shaking at 120 rpm at 25, 30, 35, 40, 45, and 50° C. respectively. The influence of different conversion temperatures on the conversion rate was investigated. According to the detection results by HPLC, it can be seen that when the conversion temperature is most preferably 40° C., the conversion rate is 44.6% (FIG. 12e), so 40° C. can be used as the optimal conversion temperature.

(5) Conversion Time

The time in the optimized conversion conditions obtained in Step (4) was set to 1, 2, 3, 4, 5, 6, 7, 8, 9, 10, 11, 12, 13, and 14 h, and the influence of different conversion time on the conversion rate was investigated. According to the detection results by HPLC, it can be seen that when the conversion time is most preferably 10 h, the conversion rate is 45.8% (FIG. 12d), so a conversion time of 10 h can be used as the optimal conversion time.

(6) The Concentration of Calcium Ions 8 mL toluene with 8 mg/mL PC50 was taken as the organic phase for reaction and 4 mL crude enzyme solution with 40 mg/mL L-serine was taken as the aqueous phase for reaction. Calcium chloride having a final concentration of 0 mM, 5 mM, 10 mM, 15 mM, or 20 mM was added to the aqueous phase respectively. The organic phase and the aqueous phase were mixed thoroughly, and then reacted for 10 h with shaking at 120 rpm at 40° C. The production of PS was detected. When the concentration of calcium chloride is 15 mM, the conversion rate is the highest and is 48.6% (FIG. 12f), so 15 mM $CaCl_2$ can be added to the conversion system to obtain the highest conversion rate.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A transgenic cell line comprising a polynucleotide that comprises the nucleotide sequence of SEQ ID NO: 2.

2. A recombinant plasmid that comprises a gene encoding a phospholipase D, wherein said gene comprises SEQ ID NO:2, a nucleic acid encoding a signal peptide, wherein said nucleic acid comprises SEQ ID NO:3, a ribosome binding site that comprises SEQ ID NO:4, and a promoter that comprises SEQ ID NO:5.

3. The recombinant plasmid according to claim 2, wherein the recombinant plasmid is obtained by modifying the plasmid pDXW-10a that comprises SEQ ID NO:6 to introduce the gene that comprises SEQ ID NO:2, the nucleic acid encoding the signal peptide that comprises SEQ ID NO:3, the ribosome binding site that comprises SEQ ID NO:4, and the promoter that comprises SEQ ID NO:5.

4. A recombinant strain expressing a phospholipase D, wherein said recombinant strain is obtained by introducing a recombinant plasmid that comprises a gene encoding a phospholipase D, wherein said gene comprises SEQ ID NO:2, a nucleic acid encoding a signal peptide, wherein said nucleic acid comprises SEQ ID NO:3, a ribosome binding site that comprises SEQ ID NO:4, and a promoter that comprises SEQ ID NO:5.

5. The recombinant strain according to claim 4, wherein the recombinant strain is *Bacillus subtilis*, *Pichia pastoris* or *Corynebacterium glutamicum* strain.

* * * * *

SEQUENCE LISTING

<160> NUMBER OF SEQ ID NOS: 6

<210> SEQ ID NO 1
<211> LENGTH: 540
<212> TYPE: PRT
<213> ORGANISM: Artificial sequence
<220> FEATURE:
<223> OTHER INFORMATION: Phospholipase D

```
<400> SEQUENCE: 1

Met Ala Arg His Pro Arg Lys Arg Arg Ser Ala Leu Val Pro Arg Thr
1               5                   10                  15

Ala Val Pro Ala Leu Val Ala Val Leu Leu Pro Val Ala Pro Ala Ser
            20                  25                  30

Ala Asp Thr Gly Ala Thr Pro Ala Thr Pro His Leu Asp Ala Val Glu
        35                  40                  45

Gln Thr Leu Arg Gln Val Ser Pro Gly Leu Glu Gly Arg Val Trp Glu
    50                  55                  60

Arg Thr Ala Gly Asn Thr Leu Asp Ala Ser Thr Pro Gly Gly Ala Asp
65                  70                  75                  80

Trp Leu Leu Gln Thr Pro Gly Cys Trp Gly Asp Ala Thr Cys Ala Asp
                85                  90                  95

Arg Pro Gly Thr Arg Gln Leu Leu Val Lys Met Thr Glu Asn Val Ser
            100                 105                 110

Arg Ala Thr Glu Ser Val Asp Ile Ser Thr Leu Ala Pro Phe Pro Asn
        115                 120                 125

Gly Ala Phe Gln Asp Ala Val Val Ser Gly Leu Lys Ala Ser Val Ala
    130                 135                 140

Ser Gly His Gln Pro Lys Val Arg Ile Leu Val Gly Ala Ala Pro Ile
145                 150                 155                 160

Tyr His Leu Asn Val Val Pro Ser Lys Tyr Arg Asp Glu Leu Val Glu
                165                 170                 175

Lys Leu Gly Lys Asp Ala Ala Lys Val Thr Leu Asn Val Ala Ser Met
            180                 185                 190

Thr Thr Ser Lys Thr Ala Phe Ser Trp Asn His Ser Lys Leu Leu Val
        195                 200                 205

Val Asp Gly Arg Ser Ala Ile Thr Gly Gly Ile Asn Gly Trp Lys Asp
    210                 215                 220

Asp Tyr Leu Asp Thr Thr His Pro Val Ser Asp Val Asp Leu Ala Leu
225                 230                 235                 240

Ser Gly Pro Ala Ala Ala Ser Ala Gly Lys Tyr Leu Asn Glu Leu Trp
                245                 250                 255

Ser Trp Thr Cys Arg Asn Lys Asn Asn Ile Ala Ser Val Trp Phe Ala
            260                 265                 270

Ser Ser Asn Gly Ala Gly Cys Met Pro Thr Leu Glu Pro Ala Ala Ser
        275                 280                 285

Ala Glu Ala Pro Arg Gly Asp Val Pro Val Ile Ala Val Gly Gly Leu
    290                 295                 300

Gly Val Gly Ile Gln Arg Asp Asp Pro Ala Ser Arg Phe Arg Pro Thr
305                 310                 315                 320

Leu Pro Thr Ala Pro Asp Thr Lys Cys Val Val Ala Leu His Asp Asn
                325                 330                 335

Thr Asn Ala Asp Arg Asp Tyr Asp Thr Val Asn Pro Glu Glu Ser Ala
            340                 345                 350

Leu Arg Ala Leu Ile Ser Ser Ala Asp Arg His Ile Glu Ile Ser Gln
        355                 360                 365

Gln Asp Leu Asn Ala Thr Cys Pro Pro Leu Pro Arg Tyr Asp Ile Arg
    370                 375                 380

Val Tyr Asp Ala Leu Ala Ala Lys Met Ala Ala Gly Val Lys Val Arg
385                 390                 395                 400

Ile Val Val Ser Asp Pro Ala Asn Arg Gly Ala Val Gly Ser Gly Gly
```

```
              405                 410                 415
Tyr Ser Gln Ile Lys Ser Leu Thr Glu Ile Ser Asp Thr Leu Arg Asp
            420                 425                 430

Arg Leu Ala Leu Arg Thr Gly Asp Gln Ala Ser Ala Arg Thr Ala Met
            435                 440                 445

Cys Ser Asn Leu Gln Leu Ala Thr Ala Arg Ser Ser Thr Ser Pro Lys
        450                 455                 460

Trp Ala Asp Glu His Pro Tyr Ala Gln His His Lys Leu Ile Ser Val
465                 470                 475                 480

Asp Gly Ser Ala Phe Tyr Ile Gly Ser Lys Asn Leu Tyr Pro Ala Trp
                485                 490                 495

Leu Gln Asp Phe Gly Tyr Val Val Glu Ser Pro Ala Ala Lys Gln
            500                 505                 510

Leu Asp Thr His Leu Leu Ala Pro Gln Trp Gln Phe Ser Arg Asp Thr
        515                 520                 525

Ala Thr Val Asp Tyr Glu Arg Gly Ile Cys Gln Asp
        530                 535                 540

<210> SEQ ID NO 2
<211> LENGTH: 1623
<212> TYPE: DNA
<213> ORGANISM: Artificial sequence
<220> FEATURE:
<223> OTHER INFORMATION: Phospholipase D

<400> SEQUENCE: 2
atggcacgtc atccgcgcaa acgtcgctcc gcactggtgc cgcgtaccgc agttccggca      60
ctggtggctg ttctgctgcc ggtggcgccg gcctcagcag acaccggtgc aacgccggca     120
accccgcacc tggatgcggt ggaacagacc ctgcgccaag tttcgccggg cctggaaggt     180
cgtgtttggg aacgcacggc tggtaacacc ctggacgcaa gcaccccggg cggtgcagat     240
tggctgctgc agacgccggg ttgctggggt gacgcaacgt gtgctgatcg tccgggcacc     300
cgccaactgc tggttaaaat gacggaaaac gtctctcgtg caaccgaaag tgtcgacatt     360
tccacgctgc gccgtttcc gaatggtgcg ttccaggatg ccgttgttag tggcctgaaa     420
gcgagcgttg cctctggtca tcaaccgaaa gtccgtattc tggtgggcgc ggccccgatc     480
tatcacctga atgtcgtgcc gagcaaatac cgcgacgaaa ctggtgaaaa actgggtaaa     540
gatgcagcta agttaccct gaacgtcgca tcaatgacca cgtcgaaaac ggcttttagc     600
tggaatcatt ctaaactgct ggttgtcgat ggccgttctg cgattaccgg cggtatcaac     660
ggttggaaag atgactatct ggataccacg caccctgtga gtgatgttga cctggcactg     720
tctggtccgg cagcagcaag tgctggtaaa tacctgaacg aactgtggtc gtggaccctg     780
cgcaataaaa acaatattgc gagcgtgtgg tttgccagct ctaatggcgc aggttgtatg     840
ccgaccctgg aaccggctgc atccgctgaa gcaccgcgtg gcgatgtccc ggtgattgca     900
gtcggcggtc tgggcgtggg tatccagcgt gatgacccgg ccagccgttt ccgtccgacg     960
ctgccgaccg caccggacac caaatgcgtg gttgcgctgc atgataacac caatgccgat    1020
cgtgactacg atacggtgaa cccggaagaa tctgcactgc gtgctctgat cagttccgcg    1080
gaccgccaca ttgaaatcag tcagcaagat ctgaatgcca cctgtccgcc gctgccgcgt    1140
tatgacattc gcgtgtacga tgcgctggcg gcaaaaatgg ctgcgggcgt taaagtccgt    1200
atcgtcgtga gcgatccggc aaaccgtggt gctgttggta gtggcggtta ttcccagatt    1260
aaatcactga cggaaatcag cgacaccctg cgtgatcgtc tggcactgcg taccggtgat    1320
```

```
caggcctccg cacgtacggc aatgtgctca aacctgcaac tggctacggc gcgctcatcg    1380
acctctccga aatgggcaga cgaacatccg tatgctcagc atcacaaact gatttcggtg    1440
gatggcagcg catttatat cggttccaaa aatctgtacc cggcctggct gcaggatttc     1500
ggctacgttg tcgaatcacc ggccgcagct aaacaactgg atacccacct gctggcgccg    1560
cagtggcaat tcagtcgtga caccgccacg gttgattatg aacgcggtat tgtcaggat    1620 taa                                                                 1623

<210> SEQ ID NO 3
<211> LENGTH: 96
<212> TYPE: DNA
<213> ORGANISM: Artificial sequence
<220> FEATURE:
<223> OTHER INFORMATION: Signal peptide gene

<400> SEQUENCE: 3
atgaaaaaaa gaaagaggcg aaactttaaa aggttcattg cagcattttt agtgttggct    60
ttaatgattt cattagtgcc agccgatgta ctagca                              96

<210> SEQ ID NO 4
<211> LENGTH: 15
<212> TYPE: DNA
<213> ORGANISM: Artificial sequence
<220> FEATURE:
<223> OTHER INFORMATION: Ribosome binding site

<400> SEQUENCE: 4
agaaggagat atacc                                                     15

<210> SEQ ID NO 5
<211> LENGTH: 372
<212> TYPE: DNA
<213> ORGANISM: Artificial sequence
<220> FEATURE:
<223> OTHER INFORMATION: Promoter

<400> SEQUENCE: 5 attttatca acgaaattta tttcaatcat tgtatttctc gaccccgctg tcgcgatcgt     60
gctcgatacc gtcttcacag gcttccgccc tgacctctat caaacgcttg gcatcgtaat    120
gatctttgcg ggcatggcct tgacgcttgt caggaggcag gggaaggcga atgtgacagc    180
tgagggtacg gatattgaac aaatacaata aaaaatgtaa aaaggcctat gcggcctttt    240
tttgttttag gtcaattgac tctcgctaat ccttaaaata agataaattt ctagaaaaaa    300
tattgtaatg atatttcagt ctagttaaga ttattgagta aatattactt ttattacaaa    360
aggagagagg aa                                                        372

<210> SEQ ID NO 6
<211> LENGTH: 8351
<212> TYPE: DNA
<213> ORGANISM: Artificial sequence
<220> FEATURE:
<223> OTHER INFORMATION: pDXW-10a starting plasmid

<400> SEQUENCE: 6
gaattcgcta gcgagctccc atgggcggcc gcctcgaggg aaccagatct ccgcggctta    60
agctgcagaa gcttctgttt tggcggatga gagaagattt tcagcctgat acagattaaa    120
tcagaacgca gaagcggtct gataaaacag aatttgcctg gcggcagtag cgcggtggtc    180
```

```
ccacctgacc ccatgccgaa ctcagaagtg aaacgccgta gcgccgatgg tagtgtgggg    240
tctccccatg cgagagtagg gaactgccag gcatcaaata aaacgaaagg ctcagtcgaa    300
agactgggcc tttcgtttta tctgttgttt gtcggtgaac gctctcctga gtaggacaaa    360
tccgccggga gcggatttga acgttgcgaa gcaacggccc ggagggtggc gggcaggacg    420
cccgccataa actgccaggc atcaaattaa gcagaaggcc atcctgacgg atggcctttt    480
tgcgtttcta caaactcttt tgtttatttt tctaaataca ttcaaatatg tatccgctca    540
tgagacaata accctgataa atgcttcaat aatattgaaa aaggaagagt atgagtattc    600
aacatttccg tgtcgccctt attcccttt ttgcggcatt ttgccttcct gtttttgctc    660
acccagaaac gctggtgaaa gtaaaagatg ctgaagatca gttgggtgca cgagtgggtt    720
acatcgaact ggatctcaac agcggtaaga tccttgagag ttttcgcccc gaagaacgtt    780
ttccaatgat gagcactttt aaagttctgc tatgtggcgc ggtattatcc cgtgttgacg    840
ccgggcaaga gcaactcggt cgccgcatac actattctca gaatgacttg gttgagtact    900
caccagtcac agaaaagcat cttacggatg gcatgacagt aagagaatta tgcagtgctg    960
ccataaccat gagtgataac actgcggcca acttacttct gacaacgatc ggaggaccga   1020
aggagctaac cgcttttttg cacaacatgg ggatcatgta actcgccttg atcgttggg    1080 aaccggagct gaatgaagcc ataccaaacg acgagcgtga ccacgatg cctgtagcaa    1140 tggcaacaac gttgcgcaaa ctattaactg gcgaactact tactctagct tcccggcaac   1200
aattaataga ctggatggag gcggataaag ttgcaggacc acttctgcgc tcggcccttc   1260
cggctggctg gtttattgct gataaatctg gagccggtga gcgtgggtct cgcggtatca   1320
ttgcagcact ggggccagat ggtaagccct cccgtatcgt agttatctac acgacgggga   1380
gtcaggcaac tatggatgaa cgaaatagac agatcgctga gataggtgcc tcactgatta   1440
agcattggta actgtcagac caagtttact catatatact ttagattgat ttaaaacttc   1500 attttttaatt taaaaggatc taggtgaaga tccttttga taatctcatg accaaaatcc   1560
cttaacgtga gttttcgttc cactgagcgt cagaccccgt agaaaagatc aaaggatctt   1620
cttgagatcc ttttttttctg cgcgtaatct gctgcttgca acaaaaaaaa ccaccgctac   1680
cagcggtggt ttgtttgccg gatcaagagc taccaactct ttttccgaag gtaactggct   1740
tcagcagagc gcagatacca aatactgtcc ttctagtgta gccgtagtta ggccaccact   1800
tcaagaactc tgtagcaccg cctacatacc tcgctctgct aatcctgtta ccagtggctg   1860
ctgccagtgg cgataagtcg tgtcttaccg ggttggactc aagacgatag ttaccggata   1920
aggcgcagcg gtcgggctga acggggggtt cgtgcacaca gcccagcttg gagcgaacga   1980
cctacaccga actgagatac ctacagcgtg agctatgaga aagcgccacg cttcccgaag   2040
ggagaaaggc ggacaggtat ccggtaagcg gcagggtcgg aacaggagag cgcacgaggg   2100
agcttccagg gggaaacgcc tggtatcttt atagtcctgt cgggtttcgc cacctctgac   2160
ttgagcgtcg atttttgtga tgctcgtcag ggggggcggag cctatggaaa aacgccagca   2220
acgcggcctt tttacggttc ctggcctttt gctggccttt tgctcacatg ttctttcctg   2280
cgttatcccc tgattctgtg ataaccgta ttaccgcctt tgagtgagct gataccgctc   2340
gccgcagccg aacgaccgag cgcagcgagt cagtgagcga ggaagcggaa gagcgcctga   2400
tgcggtattt tctccttacg catctgtgcg gtatttcaca ccgcatatgg tgcactctca   2460
gtacaatctg ctctgatgcc gcatagttaa gccagtatac actccgctat cgctacgtga   2520
ctgggtcatg gctgcgcccc gacacccgcc aacacccgct gacgcgccct gacgggcttg   2580
```

-continued

```
tctgctcccg gcatccgctt acagacaagc tgtgaccgtc tccgggagct gcatgtgtca    2640
gaggttttca ccgtcatcac cgaaacgcgc gaggcagctg cggtaaagct catcagcgtg    2700
gtcgtgaagc gattcacaga tgtctgcctg ttcatccgcg tccagctcgt tgagtttctc    2760
cagaagcgtt aatgtctggc ttctgataaa gcgggccatg ttaagggcgg ttttttcctg    2820
tttggtcact tgatgcctcc gtgtaagggg gaatttctgt tcatgggggt aatgataccg    2880
atgaaacgag agaggatgct cacgatacgg gttactgatg atgaacatgc ccggttactg    2940
gaacgttgtg agggtaaaca actggcggta tggatgcggc gggaccagag aaaaatcact    3000
cagggtcaat gccagcgctt cgttaataca gatgtaggtg ttccacaggg tagccagcag    3060
catcctgcga tgcagatccg gaacataatg gtgcagggcg ctgacttccg cgtttccaga    3120
ctttacgaaa cacggaaacc gaagaccatt catgttgttg ctcaggtcgc agacgttttg    3180
cagcagcagt cgcttcacgt tcgctcgcgt atcggtgatt cattctgcta accagtaagg    3240 caacccccgcc agcctagccg ggtcctcaac gacaggagca cgatcatgcg cacccgtggc    3300
caggacccaa cgctgcccga tgcgccgc gtgcggctgc tggagatggc ggacgcgatg    3360
gatatgttct gccaagggtt ggtttgcgca ttcacagttc tccgcaagaa ttgattggct    3420
ccaattcttg gagtggtgaa tccgttagcg aggtgccgcc ggcttccatt caggtcgagg    3480
tggcccggct ccatgcaccg cgacgcaacg cggggaggca gacaaggtat agggcggcgc    3540
ctacaatcca tgccaacccg ttccatgtgc tcgccgaggc ggcataaatc gccgtgacga    3600
tcagcggtcc agtgatcgaa gttaggctgg taagagccgc gagcgatcct tgaagctgtc    3660
cctgatggtc gtcatctacc tgcctggaca gcatggcctg caacgcgggc atcccgatgc    3720
cgccggaagc gagaagaatc ataatgggga aggccatcca gcctcgcgtc gcgaacgcca    3780
gcaagacgta gcccagcgcg tcggccgcca tgccggcgat aatggcctgc ttctcgccga    3840
aacgtttggt ggcgggacca gtgacgaagg cttgagcgag ggcgtgcaag attccgaata    3900
ccgcaagcga caggccgatc atcgtcgcgc tccagcgaaa gcggtcctcg ccgaaaatga    3960
cccagagcgc tgccggcacc tgtcctacga gttgcatgat aaagaagaca gtcataagtg    4020
cggcgacgat agtccattgt caacaacaag acccatcata gtttgccccc gcgacattga    4080
ccataaattc atcgcacaaa atatcgaacg ggtttatgc cgcttttagt gggtgcgaag    4140
aatagtctgc tcattacccg cgaacaccgc cgcattcaga tcacgcttag tagcgtcccc    4200
atgagtaggc agaaccgcgt ccaagtccac atcatccata cgatcatgc acggggtgga    4260 atccacaccc agacttgcca gcacctcatt agcgacacgt gcgcagcgg ccacgtcctt    4320 agccttatcc acgcaatcta aacgtactg cctaaccgcg aaatcagact gaatcagttt    4380
ccaatcatcg gcttcacca aagcaacagc aacgcgggtt gattcgaccc gttccggtgc    4440
ttccagaccg gcgagcttgt acagttcttc ttccatttca cgacgtacat cagcgtctat    4500
gtaatcaatg cccaaagcac gcttagcccc acgtgaccag gacgaacgca ggttttttaga    4560 accaacctca tactcacgcc accgagccac caaaacagcg tccatatcct cgccggcgtc    4620
gctttgatcg gccaacatat ccaacatctg aaacggcgtg tacgaccct tagacgcggt    4680 tttagtagcg gagccagtca gttcctgaga catgcccta gcgaggtagg ttgccatttt    4740
cgcagcgtct ccaccccagg tagacacctg atcaagtttg accccgtgct cacgcagtgg    4800
cgcgtccata ccggccttaa ccacaccagc agaccagcgg gaaaacatgg aatcctcaaa    4860
cgccttgagt tcatcgtcag acagtggacg atccaagaac aacagcatgt tgcggtgcaa    4920
```

```
gtgccaaccg ttcgcccaag agtctgtgac ctcatagtca ctataggtgt gctccacccc   4980
gtaccgtgca cgttctttct tccactgaga tgttttcacc atcgaagagt acgcagtctt   5040
aatacccgct tcaacctgcg caaatgactg tgagcggttg tgtcgaacag tgcccacaaa   5100
catcatgagc gcgccacccg ccgccaagtg attcttagta gcaatagcca gctcaatgcg   5160
gcgttcgccc atgacttcca attcagccag aggtgacccc cagcgagagt gagagttttg   5220
cagaccctca aactgcgaag caccgttaga cgaccaggac accgaacag cttcgtccct   5280 gcgccaccta tggcaccccg ccagagcctt actattggtg atcttgtaca tgacgttttg   5340
cctacgccac gccctagcgc gagtgacctt agaaccctca ttgacctgcg gttccttaga   5400
ggtgttcact tctatttcag tgttacctag acccgatgtt gtgcggggtt gcgcagtgcg   5460
agtttgtgcg ggtgttgtgc ccgttgtctt agctagtgct atggttgtca attgaaaccc   5520
cttcgggtta tgtggccccc gtgcatatga gttggtagct cgcacggggg tttgtcttgt   5580
ctagggacta ttaatttta gtggtgtttg gtggccgcct agcttggcta tgcgtgccag   5640
cttacccgta ctcaatgtta aagatttgca tcgacatggg agggttacgt gtccgatacc   5700 taggggggt atccgcgact aggtgccccg gtgctcactg tctgtaccgg cggggcaagc   5760
cccacacccc gcatggacag ggtggctccg cccctgcac cccagcaat ctgcatgtac   5820 atgttttaca cattagcacg acatgactgc atgtgcatgc actgcatgca gactaggtaa   5880
atatgagtat gtacgactag taacaggagc actgcacata atgaatgagt tgcaggacaa   5940
tgtttgctac gcatgcgcat gacatatcgc aggaaagcta ctagagtctt aaagcatggc   6000
aaccaaggca cagctagaac agcaactaca agaagctcaa caggcactac aggcgcagca   6060
agcgcaggca caagccacca tcgaagcact agaagcgcag gcaaaggcta agcccgtcgt   6120
ggtcaccgca cgcgttcctt tggcactacg tgaggacatg aagcgcgcag gcatgcagaa   6180
cggtgaaaac ctccaagagt tcatgatcgc cgcgtttacc gagcggctag aaaagctcac   6240
caccaccgac aacgaggaaa acaatgtcta acccactagt tctctttgcc caccgtgacc   6300
cggtaaatga cgtgacgttc gagtgcattg agcacgccac ctacgacaca ctttcacacg   6360
ctaaagacca gatcaccgcc caaatgcaag ccctagacga agaagccgcc ctactgccct   6420
aatgggtgtt tcatgggtgt ttccctagtg tttcatggtg ttttcaccta agctagggaa   6480
ttgcgcgaga agtctcgcaa aaatcagcaa ccccccggaac cacacagttc acggggttc   6540 ttctatgcca gaaatcagaa agggggaacca gtgaacgacc ccgaatattg gatcacagcg   6600
cagcaggtcg ccgcccgcgt agctctcacc ccggccacca ttaaaaagtg ggcaaacgag   6660
ggaaaaatca ccgcatacaa gatcggcaag tccgtccgat tcaaagcatc agacgtagac   6720
gacgatagtc atgccccgcg cccaccggaa ggagctgact gggttgaagg ctctcaaggg   6780
catcggtcga cgctctccct tatgcgactc ctgcattagg aagcagccca gtagtaggtt   6840
gaggccgttg agcaccgccg ccgcaaggaa tggtgcatgc aaggagatgg cgcccaacag   6900 tccccggcc acggggcctg ccaccatacc cacgccgaaa caagcgctca tgagcccgaa   6960
gtggcgagcc cgatcttccc catcggtgat gtcggcgata taggcgccag caaccgcacc   7020
tgtggcgccg tgtcaggtg gcactttcg gggaaatgtg cgcggaaccc ctatttgttt   7080
atttttctaa atacattcaa atatgtatcc gctcatgaat taattcttag aaaaactcat   7140
cgagcatcaa atgaaactgc aatttattca tatcaggatt atcaataccc tattttgaa   7200 aaagccgttt ctgtaatgaa ggagaaaact caccgaggca gttccatagg atggcaagat   7260
cctggtatcg gtctgcgatt ccgactcgtc caacatcaat acaacctatt aatttcccct   7320
```

-continued

```
cgtcaaaaat aaggttatca agtgagaaat caccatgagt gacgactgaa tccggtgaga    7380
atggcaaaag tttatgcatt tctttccaga cttgttcaac aggccagcca ttacgctcgt    7440
catcaaaatc actcgcatca accaaaccgt tattcattcg tgattgcgcc tgagcgagac    7500
gaaatacgcg atcgctgtta aaaggacaat tacaaacagg aatcgaatgc aaccggcgca    7560
ggaacactgc cagcgcatca acaatatttt cacctgaatc aggatattct tctaatacct    7620
ggaatgctgt tttcccgggg atcgcagtgg tgagtaacca tgcatcatca ggagtacgga    7680
taaaatgctt gatggtcgga agaggcataa attccgtcag ccagtttagt ctgaccatct    7740
catctgtaac atcattggca acgctacctt tgccatgttt cagaaacaac tctggcgcat    7800
cgggcttccc atacaatcga tagattgtcg cacctgattg cccgacatta tcgcgagccc    7860
atttataccc atataaatca gcatccatgt tggaatttaa tcgcggccta gagcaagacg    7920
tttcccgttg aatatggctc ataacacccc ttgtattact gtttatgtaa gcagacagtt    7980
ttattgttca tgaccaaaat cccttaacgt gagttttcgt tccactgagc gtcagacccc    8040
gtagaaaaga tcaaagcgcc ggtgatgccg gccacgatgc gtccggcgta gaggatccgg    8100
agcttatcga ctgcacggtg caccaatgct tctggcgtca ggcagccatc ggaagctgtg    8160
gtatggctgt gcaggtcgta aatcactgca taattcgtgt cgctcaaggc gcactcccgt    8220
tctggataat gttttttgcg ccgacatcat aacggtaccg gcaaatattc tgaaatgagc    8280
tgttgacaat taatcatcgg ctggaaccat gtgtggaatt gtgagcggat aacaatttca    8340
cacaggaaac a                                                         8351
```